US007926743B2

(12) United States Patent
Leer

(10) Patent No.: US 7,926,743 B2
(45) Date of Patent: Apr. 19, 2011

(54) PRESSURIZED TANK SPRAYER WITH FOOTSTAND

(75) Inventor: Rick L. Leer, Somerset, PA (US)

(73) Assignee: Robert Bosch GmbH, Stuttgart (DE)

( * ) Notice: Subject to any disclaimer, the term of this patent is extended or adjusted under 35 U.S.C. 154(b) by 138 days.

(21) Appl. No.: 12/275,083

(22) Filed: Nov. 20, 2008

(65) Prior Publication Data

US 2010/0123026 A1 May 20, 2010

(51) Int. Cl.
*A61M 11/02* (2006.01)

(52) U.S. Cl. ........................................................ 239/373

(58) Field of Classification Search .................. 239/373, 239/302, 337, 338, 351, 355; 222/401, 402, 222/402.1, 401.16; 169/30, 71

See application file for complete search history.

(56) References Cited

U.S. PATENT DOCUMENTS 1,470,538 A * 10/1923 Miller .............................. 33/9 A
2,559,168 A 7/1951 Numbers
2,653,618 A 9/1953 Frank
3,174,658 A * 3/1965 Wittenberg et al. ........ 222/386.5
3,485,180 A 12/1969 Wickenberg et al.
3,527,269 A 9/1970 Wilton
3,527,270 A 9/1970 Weil
4,192,464 A * 3/1980 Chow ............................ 239/373
4,767,027 A 8/1988 Lewinter et al.
4,930,686 A 6/1990 Ellison
5,072,884 A 12/1991 Ellison et al.
5,102,052 A 4/1992 Demarest et al.
5,186,391 A 2/1993 Roueche et al.
5,295,610 A 3/1994 Levison
5,363,666 A * 11/1994 Tieken ............................ 62/129
5,398,852 A 3/1995 Lacy
5,449,278 A 9/1995 Lin
5,667,106 A 9/1997 Robbins, III
5,681,154 A 10/1997 Yang
5,702,239 A 12/1997 Yang
6,065,947 A 5/2000 Wu
6,299,420 B1 10/2001 Saputo et al.
6,648,615 B2 11/2003 Tsai
6,695,228 B2 2/2004 Odessa
2006/0249223 A1 11/2006 Leer et al.

* cited by examiner

*Primary Examiner* — David Hwu
(74) *Attorney, Agent, or Firm* — Maginot, Moore & Beck

(57) ABSTRACT

A spray pump includes a tank configured to receive fluid through an opening in the tank, and a removable cap covering the opening in the tank. Attached to the cap is a first handle extending outwardly from a first side of the cap, a second handle extending outwardly from a second side of the cap opposite the first side. The spray pump further includes a removable pump operable to advance air into the tank to pressurize the tank. To stabilize the spray pump during the pressurization process, the tank includes a base portion having a first lateral foot contact portion extending outward from a first side of the tank, and a second lateral foot contact portion extending outward from a second side of the tank opposite the first side.

9 Claims, 12 Drawing Sheets

PRESSURIZED TANK SPRAYER WITH FOOTSTAND

FIELD OF THE INVENTION

The present invention relates to fluid dispensing devices and more particularly to pressurized tank sprayers.

BACKGROUND OF THE INVENTION

Pressurized tank sprayers, also referred to as pressure sprayers, are often utilized to dispense low viscosity liquids. The typical pressure sprayer consists of a tank or container for holding a solution, a hand pump, and a spray wand with a discharge valve. In operation, a person partially fills the tank with a solution leaving a portion of the tank unfilled. Next, the user attaches a hand pump to the tank. As the user strokes the hand pump, the pump mechanism forces air from outside the tank into the portion of the tank unoccupied by the solution, causing the air pressure in the tank to become greater than the atmospheric pressure outside of the tank. When a user triggers the discharge valve on the spray wand, the increased pressure within the tank propels the solution from the tank through a nozzle that terminates the spray wand. The pressure sprayer will continue to propel solution from the tank until the air pressure in the tank approximately equals the atmospheric pressure outside the tank. Then the user must again stroke the pump to redevelop the increased pressure within the tank.

Typical pressure sprayer hand pumps must be repeatedly stroked in order to generate a pressure sufficient to propel solution from the container. When numerous strokes are required to pressurize the sprayer, the user may become tired and consider the pressurization process a bother. Accordingly, it would be desirable to provide a pressure sprayer that could be more easily pressurized. It would also be advantageous if such pressure sprayer could be easily stabilized during the pressurization process and at other times when the user is working with the sprayer.

SUMMARY

A pressure sprayer includes a tank configured to receive fluid through an opening in the tank, and a removable cap covering the opening in the tank. Attached to the cap are a first handle extending outwardly from a first side of the cap and a second handle extending outwardly from a second side of the cap opposite the first side. The cap includes a passage leading to the opening in the tank. The pressure sprayer further includes a removable pump that engages the cap, wherein the pump is operable to advance air into the tank to pressurize the tank on both an upstroke and a downstroke.

To stabilize the spray pump during the pressurization process, the tank includes a base portion having a first lateral foot contact portion extending outward from a first side of the tank, and a second lateral foot contact portion extending outward from a second side of the tank opposite the first side. The first and second lateral foot contact portions are arranged and dimensioned such that a substantial portion of a man's feet may be placed on the first and second lateral foot contact portions when the man is in a standing position.

DETAILED DESCRIPTION

Figure 1:
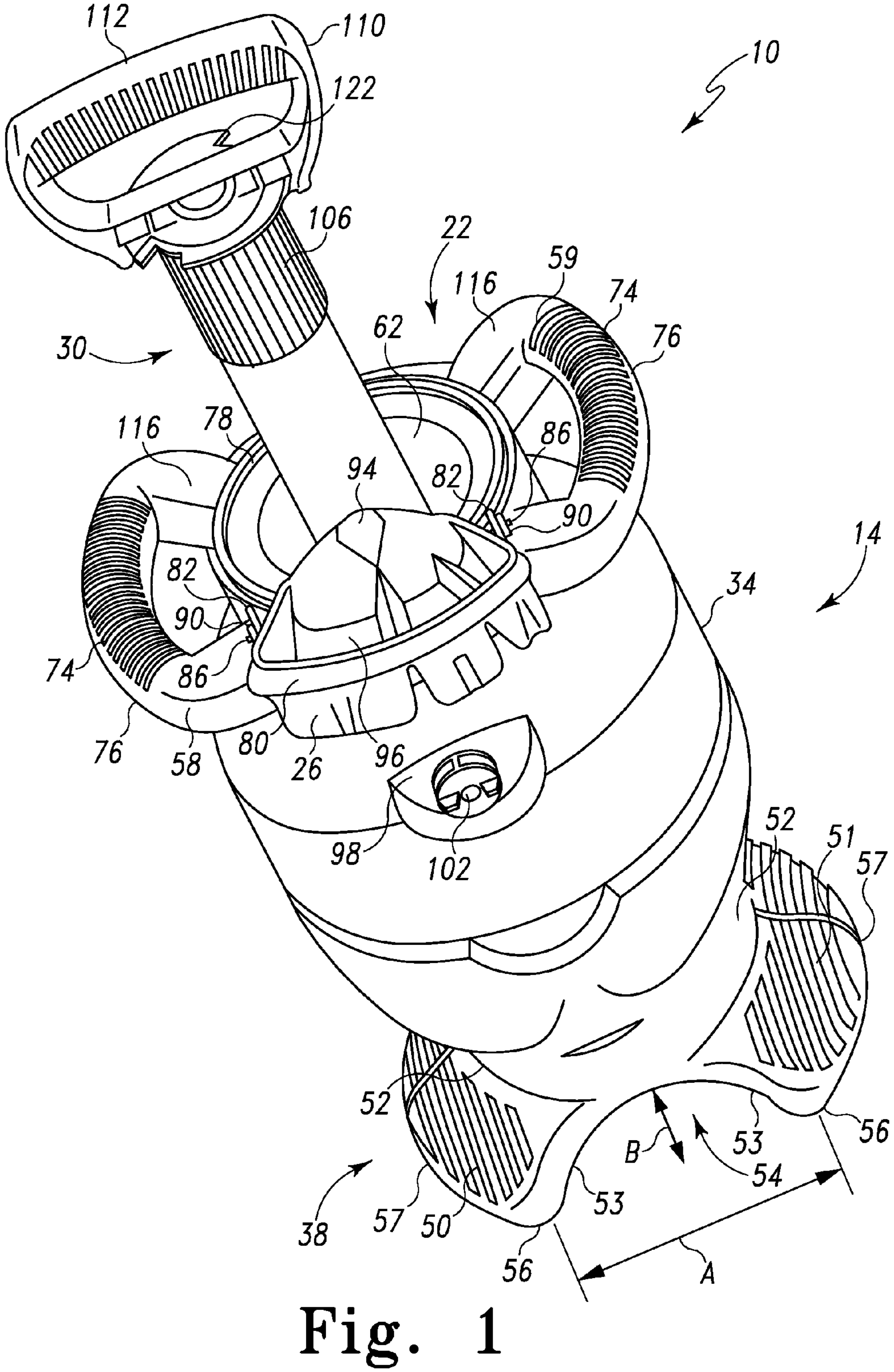
FIG. 1 depicts a perspective view of a pressurized tank sprayer.
Figure 2:
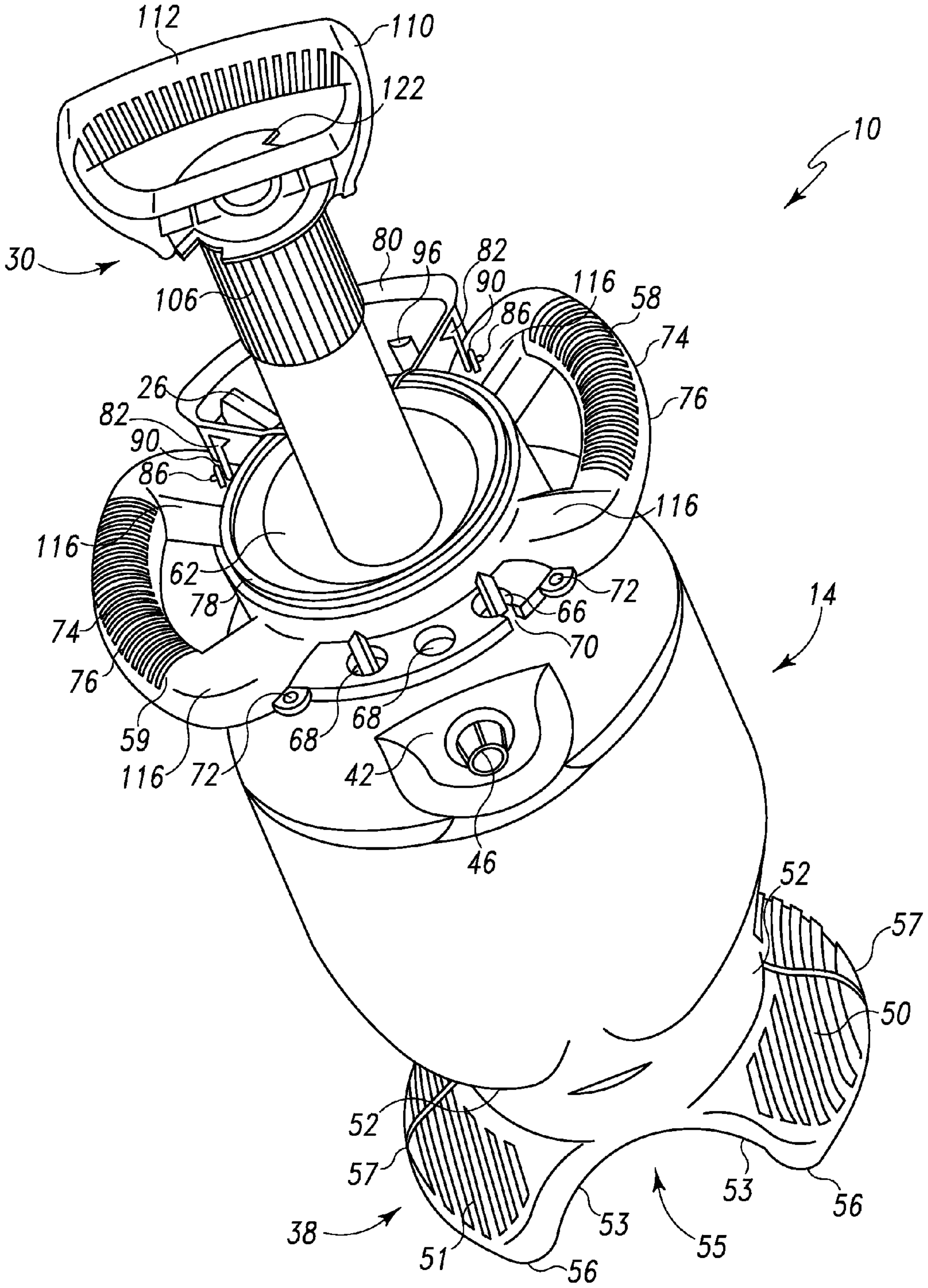
FIG. 2 depicts another perspective view of the pressurized tank sprayer of FIG. 1.

Referring to FIGS. 1 and 2, the pressurized tank sprayer 10 includes a tank 14, cap 22, measuring cup 26, and double action pump 30. The tank 14 includes a container 34 and a base 38. The container 34 and base 38 may be distinct elements or the tank 14 may be constructed in one integral unit. The container 34 forms the portion of the tank 14 that holds the solution to be sprayed. As illustrated in FIGS. 1 and 2, the container 34 has a generally substantially cylindrical shape which may also take the form of a slightly ellipsoidal shape to prevent the container 34 from becoming bowed or distorted when subject to air pressure. The container 34 is formed from a durable material that can withstand air pressure stress; including, polypropylene, polyethylene, and nylon. Embodiments of the container 34 formed from a generally opaque material may have measuring indicia on the interior surface of the container 34 visible from the opening 36 in the top of the container 34. Embodiments of the container 34 formed from a generally translucent material may include measuring indicia on the exterior of the container 34. The volume of the container 34 may vary depending on the embodiment and purpose of the sprayer.

Figure 3:
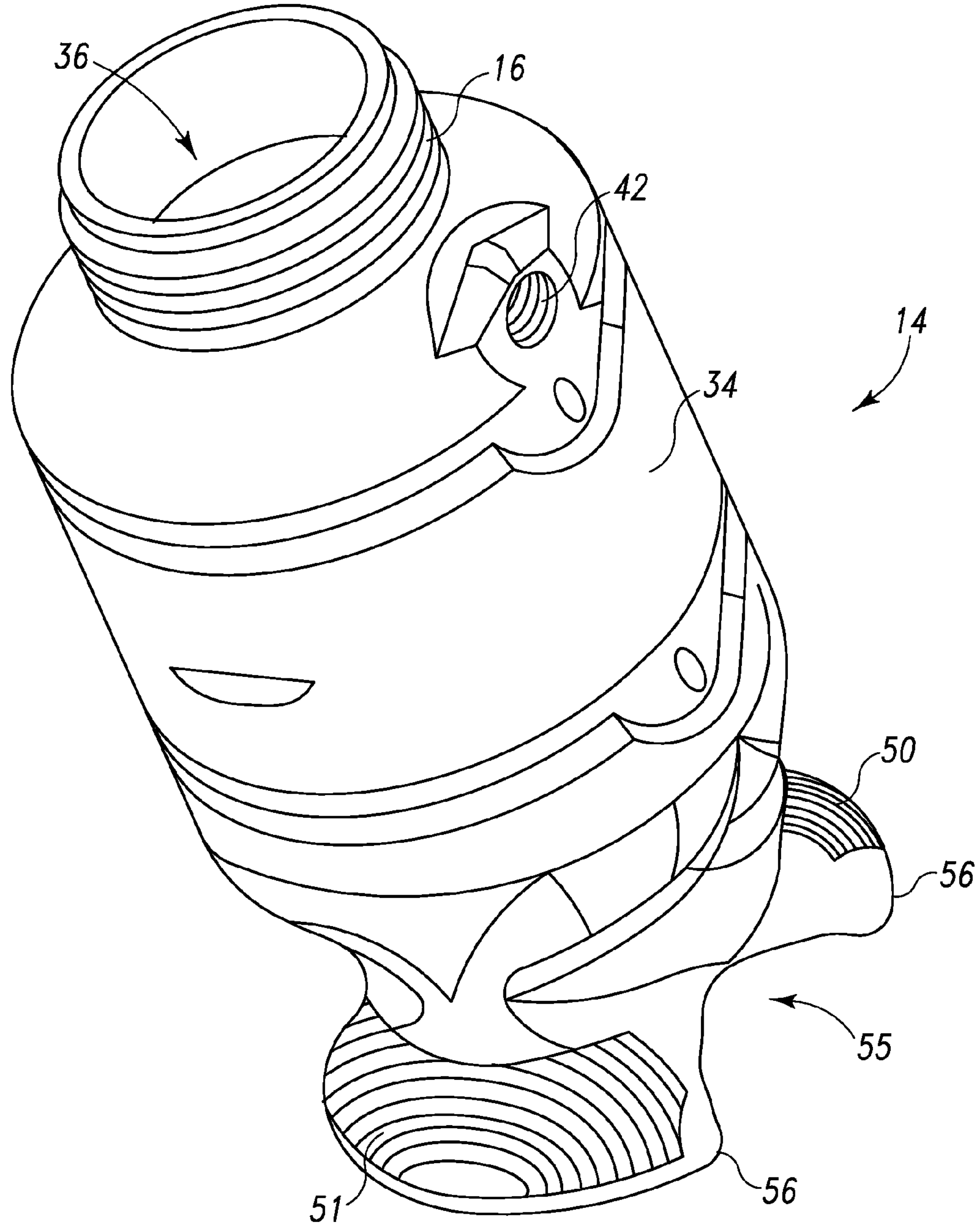
FIG. 3 depicts a perspective view of the tank of the pressurized tank sprayer of FIG. 1.

As shown in FIG. 3, the top portion of the container 34 includes a cylindrical rim 16 with an opening 36. The cylindrical rim 16 may extend upward from the container 34 and included a threaded exterior surface, as illustrated in FIG. 3. Alternatively, the cylindrical rim 16 may extend into the container 34 and include a threaded interior surface. The cylindrical rim 16 mates with an opposing threaded portion 24 of the cap 22, illustrated in FIG. 5A. The opening 36 in the cylindrical rim 16 may have a diameter large enough for a user to insert his or her adult hand into the container 34.

With reference to FIG. 2, the container 34 includes a spray port 42 that accepts a spray wand outlet 46. The spray wand outlet 46 may be secured to the spray port 42 with any suitable airtight and watertight sealing method, including a threaded engagement, epoxy, or an adhesive. As illustrated in FIG. 3 the spray port 42 includes an opening in fluid communication with the container 34. With continued reference to FIG. 2, the container 34 may contain an outlet 46 integral with the container 34 sidewalls. The outlet 46 includes a hose connection portion and a tube connection portion. The hose connection portion is on the exterior of the tank 14 and mates with the spray wand hose (not illustrated), of a typical spray wand as known in the art. The tube connection portion is on the interior of the tank 14 and mates with a pick-up tube within the container 34 that extends from the outlet 46 to the bottom of the container 34.

Figure 4:
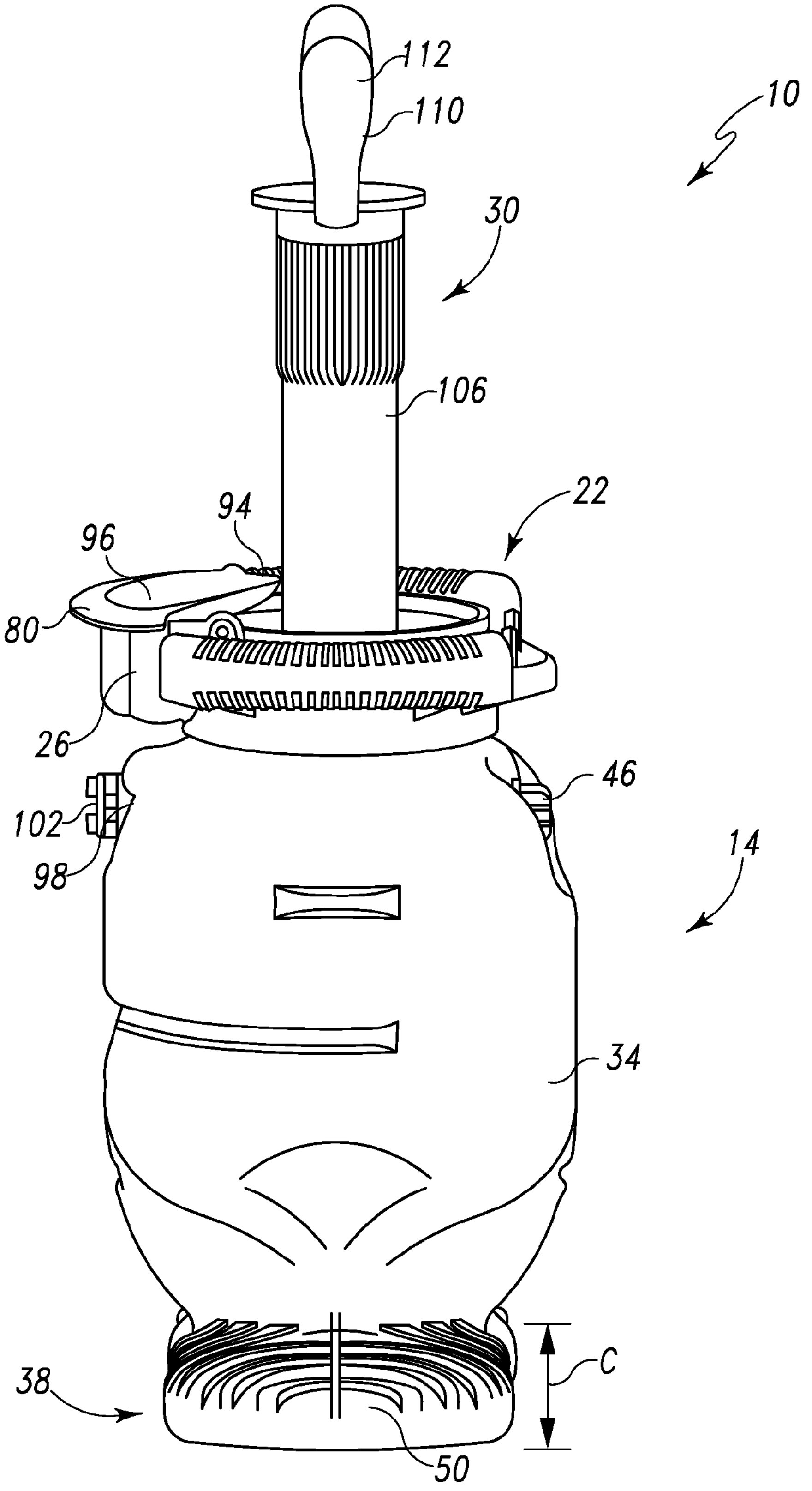
FIG. 4 depicts a side view of the pressurized tank sprayer of FIG. 1.

The container 34 also includes an air pressure relief port 98 that accepts an air pressure relief valve 102, as illustrated in FIGS. 1 and 4. The air pressure relief port 98 is typically positioned on the container 34 above the maximum solution level. The air pressure relief valve 102 may be secured to the air pressure relief port 98 with any suitable airtight and watertight sealing method, including a threaded engagement, epoxy, or an adhesive. The air pressure relief valve 102 expels air when the air pressure in the container 34 exceeds a predetermined threshold. When the air pressure in the container 34 returns to a level below the threshold level the air pressure relief valve 102 automatically closes.

The base 38 portion of the tank 14 includes footholds 54, 55 situated between footstands 50, 51 as best illustrated in FIGS. 1 and 2. The base 38 can be made from the same material as the container 34; including, polypropylene, polyethylene, and nylon. If the base 38 and the container 34 are made from different materials, the base 38 should be securely fastened to the bottom of the container 34. Ideally, a user should be able to apply a strong upward force to the pump 30 without separating the base 38 from the container 34.

The base 38 includes two footstands 50, 51 that project laterally from opposite sides of the container 34, and provide first and second lateral foot contact portions, as illustrated in FIGS. 1-4. The footstands 50, 51 have a convex periphery 57. In one embodiment, the shape of the convex footstands 50, 51 may approximately match the arch portion of a person's foot. The upper surface of each footstand 50, 51 is suitable for a user to stand upon while stroking the pump 30. In one embodiment, the upper surface of the footstands 50, 51 includes a notched or ridged surface to grip the user's feet. The footstand 50, 51 may include an inclined upper surface, with the highest portion of each foothold 50, 51 proximate the container 34 and the lowest portion of each foothold 50, 51 proximate the convex periphery 57 of each foothold 50, 51. In another embodiment, the diameter of the container 34 proximate the footholds 50, 51 gradually decreases. The gradually decreasing container 34 diameter combined with the inclined upper surface of the foothold 50, 51, forms a concave region 52 that surrounds the inner portion of a user's shoe; thereby, enabling the user to stabilize the pressure sprayer while stroking the pump 30. The side surfaces of the footstands 50, 51 have a concave periphery 53 that smoothly transitions into the convex periphery 57 at a rounded corner 56. Finally, the bottom of each footstand 50, 51 includes a surface that engages the ground to support the tank sprayer 10.

The two footholds 54, 55 are positioned between the footstands 50, 51 on the base 38, as best illustrated in FIG. 1. The footholds 54, 55 are provided as recessed areas in the bottom portion of the container 34. Specifically, distance A defines the length and distance B defines the width of the footholds 54, 55. In at least one embodiment, distance A is about three to twelve inches, and distance B is about one to six inches. Preferably, distance A is about four to six inches, and distance B is about two to three inches. The height of the footholds 54, 55 is defined by the height of the footstands 50, 51 as represented by distance C in FIG. 4. In at least one embodiment, distance C is about one-half to four inches. Preferably, distance C is about one to two inches.

In the embodiment of FIGS. 1 to 4, the footholds 54, 55 are not configured to be stood upon; instead, the footholds 54, 55 are recesses bordered by a concave sidewall 53. The concave sidewalls 53 of the footholds 54, 55 are configured to engage the sides of user's shoes, and provide rotational stability to the container 34 while the user rotates the cap 22 or the pump 30. To provide a sufficient shoe contact surface, the footholds 54, 55 include an area large enough to accept the inside forefoot portion of a man's foot or shoe. The height of the sidewalls 53 of the footholds 54, 55 may be greater than the height of the sole portion of a man's shoe in order to provide a large area of engagement with the man's shoe and prevent the footstands 50, 51 from sliding under or over the user's shoes while the user attempts to rotate the cap 22 or pump 30.

Referring to FIGS. 1 and 2 the cap 22 is threadedly connected to the top portion of the container 34 to cover the opening 36 in the container. The cap 22 includes first and second handles 58, 59 with a funnel 62 positioned between the handles 58, 59. The cap 22 is made from a rigid material, preferably plastic. The handles 58, 59 and funnel 62 can be an integral unit, or each element can be individually formed and secured together. A sealing member 204 ensures that the cap 22 makes an airtight and watertight junction with the container 34, even when the container 34 is subject to air pressure, as shown in FIG. 5. Viable sealing members 204 include rubber or synthetic gaskets and o-rings.

Figure 5A:
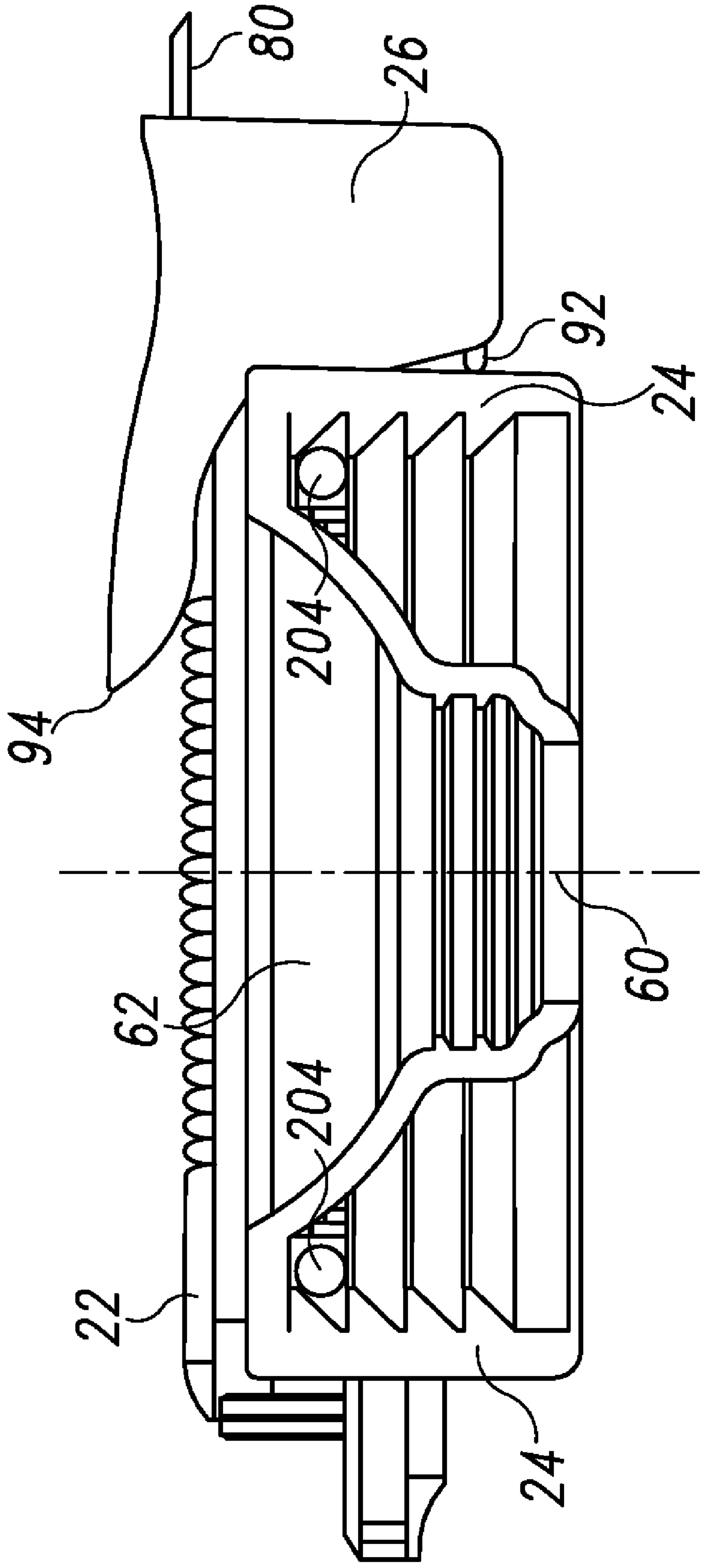
FIG. 5A depicts a cross-sectional view of the cap for the pressurized tank sprayer of FIG. 1.

The exterior periphery of the cap 22 includes a spray wand holder 66, nozzle openings 68, and strap connections 72. The spray wand holder 66 supports the spray wand when the wand is not in use. As illustrated in FIGS. 2, 5A, and 5C, the spray wand holder 66 is a circular opening in a projection extending from the cap 22. Alternatively, the spray wand holder 66 can include a circular hole with a notch 70 slightly wider than the diameter of the rigid rod portion of the spray wand. The spray wand holder 66 can be formed at any portion along the periphery of the cap 22, including in the handles 58, 59.

With continued reference to FIGS. 2, 5A, and 5C, the nozzle openings 68 provide a storage area for spray wand nozzles. As illustrated, the nozzle openings 68 extend through the periphery of the cap 22; however in another embodiment the nozzle openings 68 are depressions in the cap 22 having a bottom surface that prevents a nozzle from falling through the opening 68. The nozzle openings 68 have a conical interior surface that becomes narrower toward the bottom of the opening 68. The interior surface grips the exterior of the nozzle to prevent the nozzle from becoming inadvertently jarred from the opening 68. Furthermore, a portion of the nozzle remains above the surface of the cap 22 when the nozzle is inserted into the opening 68. The portion of the nozzle remaining above the cap 22 can be grasped by the user when the user desires to remove the nozzle from the nozzle opening 68.

The strap connections 72 provide a coupling point for the attachment members of a carrying strap. As shown in FIGS. 2, 5A, and 5C, the strap connections 72 are laterally displaced upon the cap 22 to provide the user with a balanced lifting point. Each connection 72 includes an opening that extends therethrough. The opening is sized to couple with the attachment member of a carrying strap (not illustrated). The connections 72 are sufficiently rigid to permit a user to lift and carry the tank sprayer 10 without bending or deforming the connections 72.

Also, on the exterior periphery of the cap 22 are the two laterally displaced handles 58, 59. A first handle 58 extends outwardly from a first side of the cap 22, and a second handle 59 extends outwardly from a second side of the cap 22 opposite the first side. The left and right handles 58, 59 assist the user in securing and removing the cap 22 from the container 34. The handles 58, 59 illustrated in FIGS. 1 and 2 include extension portions 116 and a horizontal connection portion 74; however, any handle 58, 59 that permits a user to apply a rotational force to the cap 22 may be utilized. For example, in one embodiment, the handles 58, 59 may include a curvature either toward or away from the base of the container 34. Depending on the shape of the container 34 the curvature may simplify grasping the handles 58, 59. In another embodiment, the handles 58, 59 extend outward in a substantially lateral direction relative to the funnel 62 such that a user's hands are positioned substantially to the sides of the funnel 62 when the tank 14 is in an upright position and the user's hands grasp the handles 58, 59. In still another embodiment, the handles 58, 59 may exhibit vertical connection portions 74. Handles 58, 59 exhibiting a vertical connection portion 74 could have substantially the same shape as the illustrated handles 58, 59 exhibiting a horizontal connection portion 74; however, each vertical connection portion 74 may include a single extension portion 116.

As illustrated in FIGS. 1 and 2, the handles 58, 59 include an irregular gripping surface 74. The gripping surface 76 reduces the likelihood that the user's gloves will slide along the surface of the handles 58, 59 as the user attempts to rotate the cap 22. As illustrated in FIG. 1, the gripping surface 76 may simply include a series of ridges in the upper and/or lower portions of the horizontal connection portions 74 grasped by the user. In another embodiment, the handles 58, 59 may include a rubberized coating instead of the series of ridges. Like the series of ridges, the rubberized coating surrounds the horizontal connection portions 74.

Figure 5B:
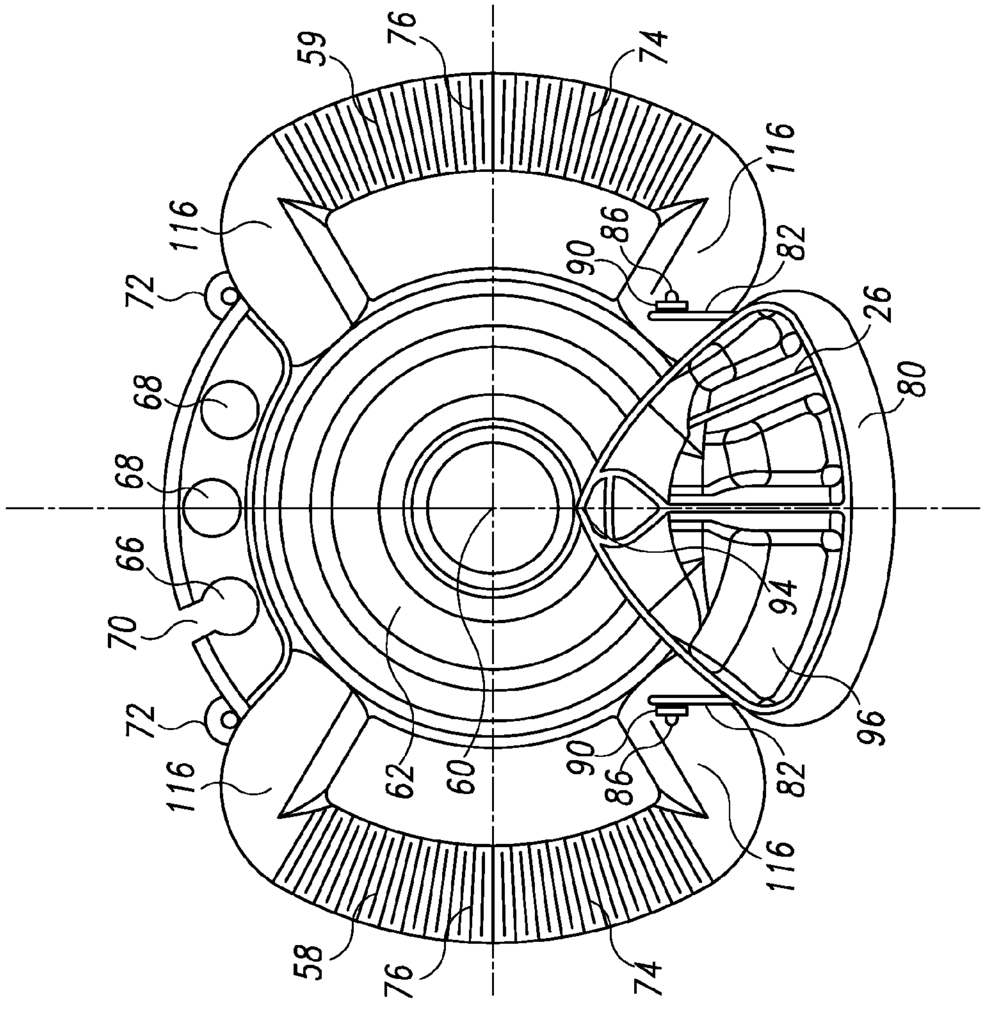
FIG. 5B depicts a top view of the cap of FIG. 5A.
Figure 5C:
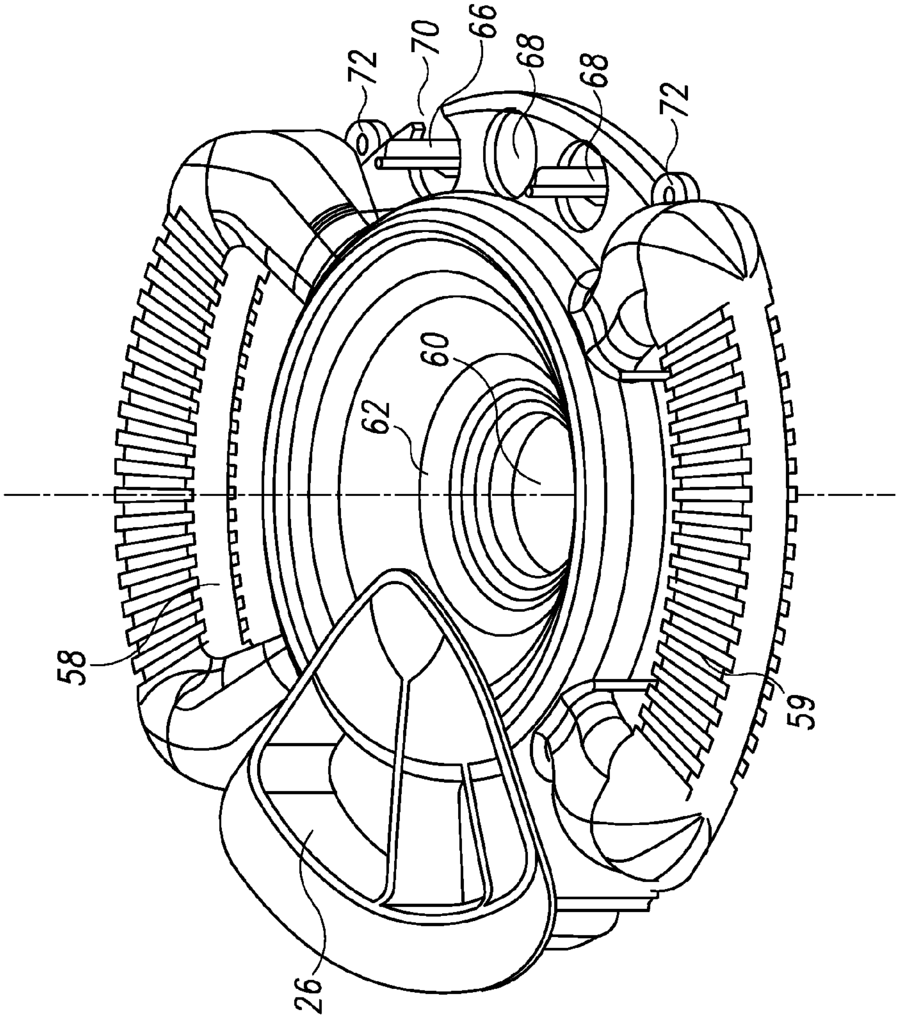
FIG. 5C depicts a perspective view of the cap of FIG. 5B.

The central portion of the cap 22 includes a funnel 62 and a drain 60 leading to the container 34, as best illustrated FIGS. 5A to 5C. The funnel 62 can be formed integrally with the cap 22, or the funnel 62 can be a distinct unit attached to the cap 22. As shown in FIGS. 5A and 5C, the drain 60 is provided as a threaded opening which provides a passage to the opening 36 in the container 34. The drain 60 is too small for a user to insert his or her adult hand. The substantially conical surface of the funnel 22 gradually becomes larger as the funnel 62 extends away from the drain 60. The top edge of the funnel 62 is terminated with a ridge 78. The depth of the funnel 62 depends on the embodiment, but in general the funnel 62 extends from the drain 60 to the top of the cap 22. In another embodiment, the top of the funnel 62 includes a cylindrical rim that extends above the cap 22 to provide the user with an even larger pouring surface. In the disclosed embodiment, the conical surface of the funnel 62 is generally smooth, without cavities or irregularities in which the funneled solution may become isolated.

A measuring vessel 26, provided in the form of a measuring cup 26, is connected to the exterior periphery of the cap 22, as shown in FIGS. 1 and 4. The measuring cup 26 is made of a rigid and sturdy material such as plastic or metal, and is suitable to measure liquid, powdered, solid, or gelled solutions. In one embodiment, the measuring cup 26 includes multiple chambers 96 of a specified quantity. For instance, the measuring cup 26 may contain chambers 96 sized to hold a tablespoon, a liquid ounce, and twenty five milliliters. Furthermore, each chamber 96 may include additional indicia that further divide the chambers 96 into smaller quantities. In another embodiment, the measuring cup 26 simply includes one large chamber 96 with indicia marked on the inner surface. In either embodiment, the measuring cup 26 can be made from a translucent material and the measuring indicia can be formed into the outer surface of the chamber 96 or chambers 96. The indicia indicate measured quantities in both Metric and United States Customary Units.

The measuring cup 26 includes arms 82 with tabs 86 that secure the first and second side of the measuring cup 26 to a pair of brackets 90, as best illustrated in FIGS. 1 and 2. The brackets 90 can be attached to, or integral with, the cap 22 or the handles 58, 59. In general, the measuring cup 26 is pivotably attached to the brackets 90; however, the measuring cup 26 can be removed and reattached by bending the resilient arms 82, thereby pulling the tabs 86 out of the brackets 90. When attached to the cap 22, the measuring cup 26 pivots about the tabs 86 from an upright "fill" position to a tilted "pour" position. The bottom portion of the measuring cup 26 includes a post 92 that rests against the periphery of the cap 22 or the container 34 to maintain the measuring cup 26 in a level orientation while the measuring cup 26 is in the fill position. When the measuring cup 26 is pivoted, the contents of each chamber 96 are directed out of the measuring cup 26 and onto the conical surface of the funnel 62, which is in fluid communication with the container 34 via the drain 60. The measuring cup 26 includes a spout 94 into which the chambers 96 divert their contents when the measuring cup 26 becomes pivoted to the pour position. The spout 94 ensures the contents of the measuring chambers 96 are accurately directed onto the conical surface of the funnel 62.

The upper periphery of the measuring cup 26 may include a ridge 80, as most clearly illustrated in FIG. 5A. The ridge 80 extends from the body of the measuring cup 26 and can be used as a handle to pivot the measuring cup 26. Additionally, in some embodiments, the ridge 80 may include measuring indicia corresponding to the capacity of the chambers 96.

As previously mentioned, the spout 94 directs the contents of the chambers 96 on to the surface of the funnel 62. Additionally, the spout 94 serves as an interlock device, as best illustrated in FIG. 4. In particular, the pump housing 106 prevents the measuring cup 26 from pivoting to the pour position when the pump housing 106 is positioned in the drain 60 of the cap 22. Motion is prevented because the spout 94 abuts the housing 106 of the pump 30 when the pump 30 is connected to the drain 60 in the cap 22. The housing 106 prevents the measuring cup 26 from pivoting, because in order to pivot the spout 94 must move toward the center of the drain 60; however, with the pump housing 106 in the path of movement, the spout 94 cannot move toward the drain 60. Of course, with the pump 30 removed from the drain 60, the path of movement of the measuring cup 26 is unobstructed, permitting the measuring cup 26 to pivot to the tilted "pour" position.

Figure 6:
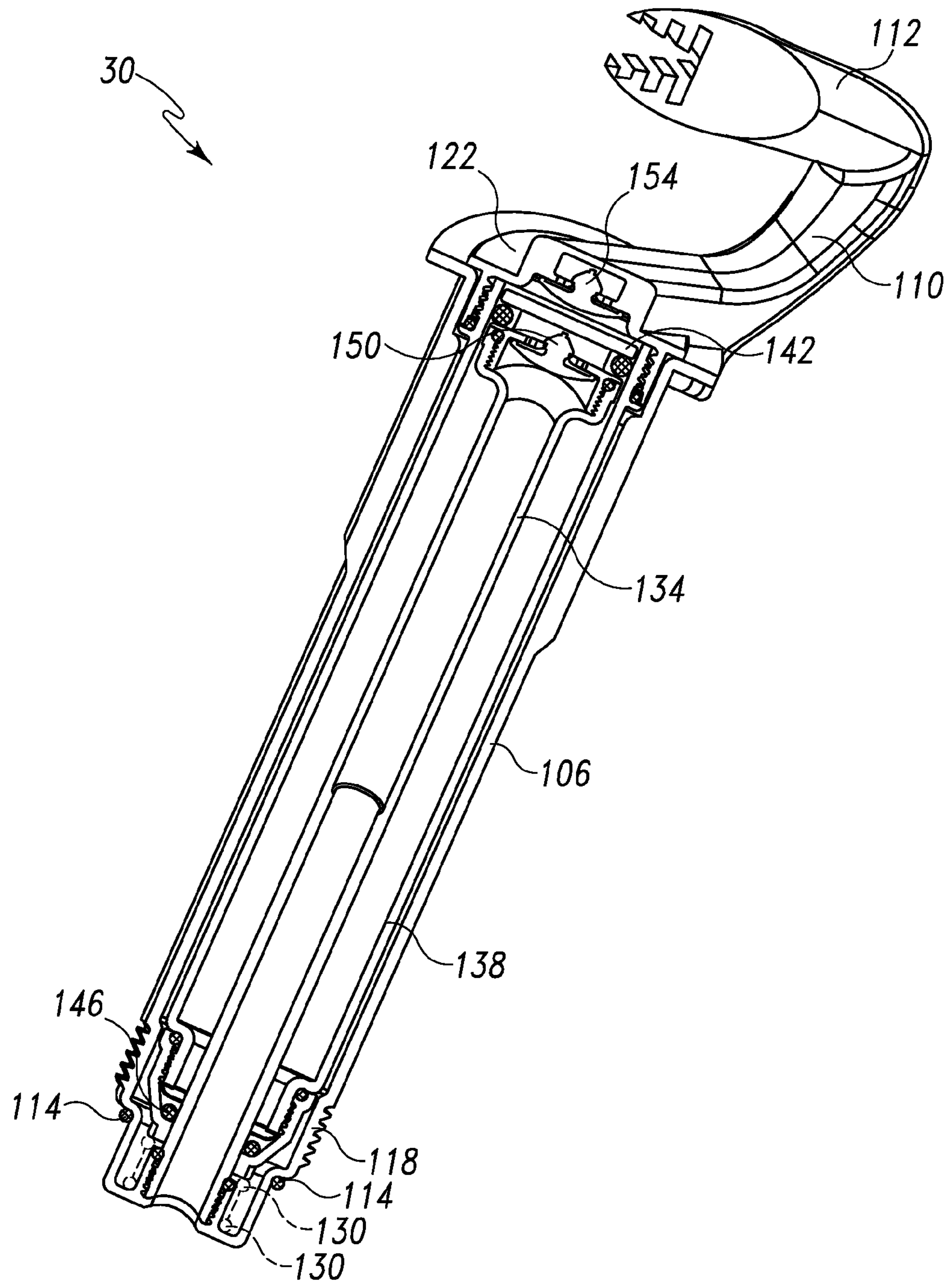
FIG. 6 depicts a cross-sectional view of a double action hand pump of the pressurized tank sprayer of FIG. 1.

The double action pump 30 includes an outer housing 106, a pump mechanism, and a handle 110, as illustrated in FIG. 6. The housing 106 is made of a rigid material, usually plastic or metal. In one embodiment, the housing 106 has a cylindrical shape, with a diameter that abuts the spout 94 of the measuring cup 26 when the measuring cup 26 is in the fill position. In another embodiment, the housing 106 includes a spout receptor that engages the spout 94 once the housing 106 has been completely threaded into the drain 60 in the cap 22. The spout receptor can be a spout 94 shaped indentation in the housing 106 that receives the spout 94 when the pump 30 is securely fastened to the cap 22. In each embodiment, the housing 106 prevents the measuring cup 26 from pivoting when the pump 30 is attached to the cap 22.

Figure 7:
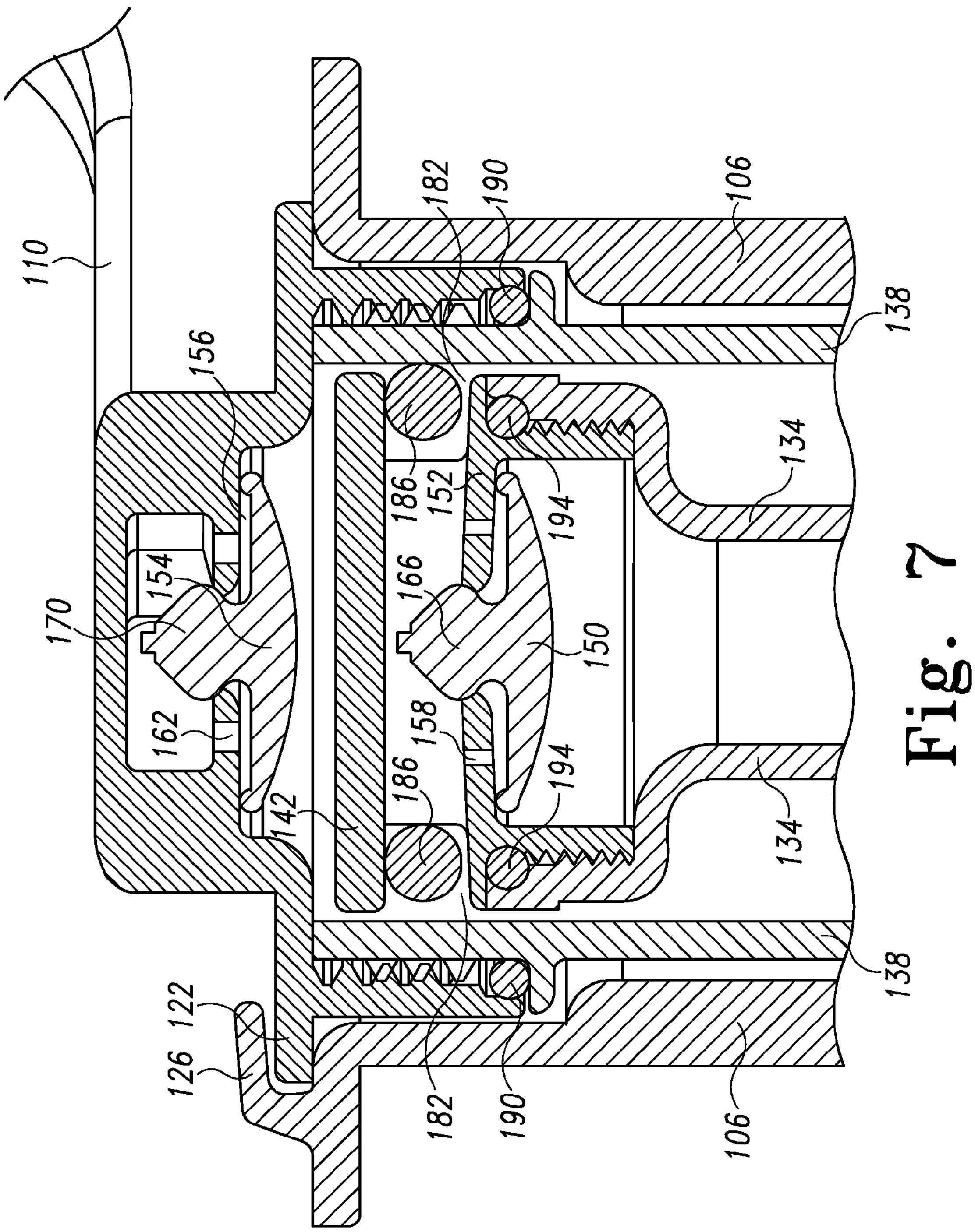
FIG. 7 depicts a cross-sectional view of an upper portion of the double action hand pump of FIG. 6.
Figure 8:
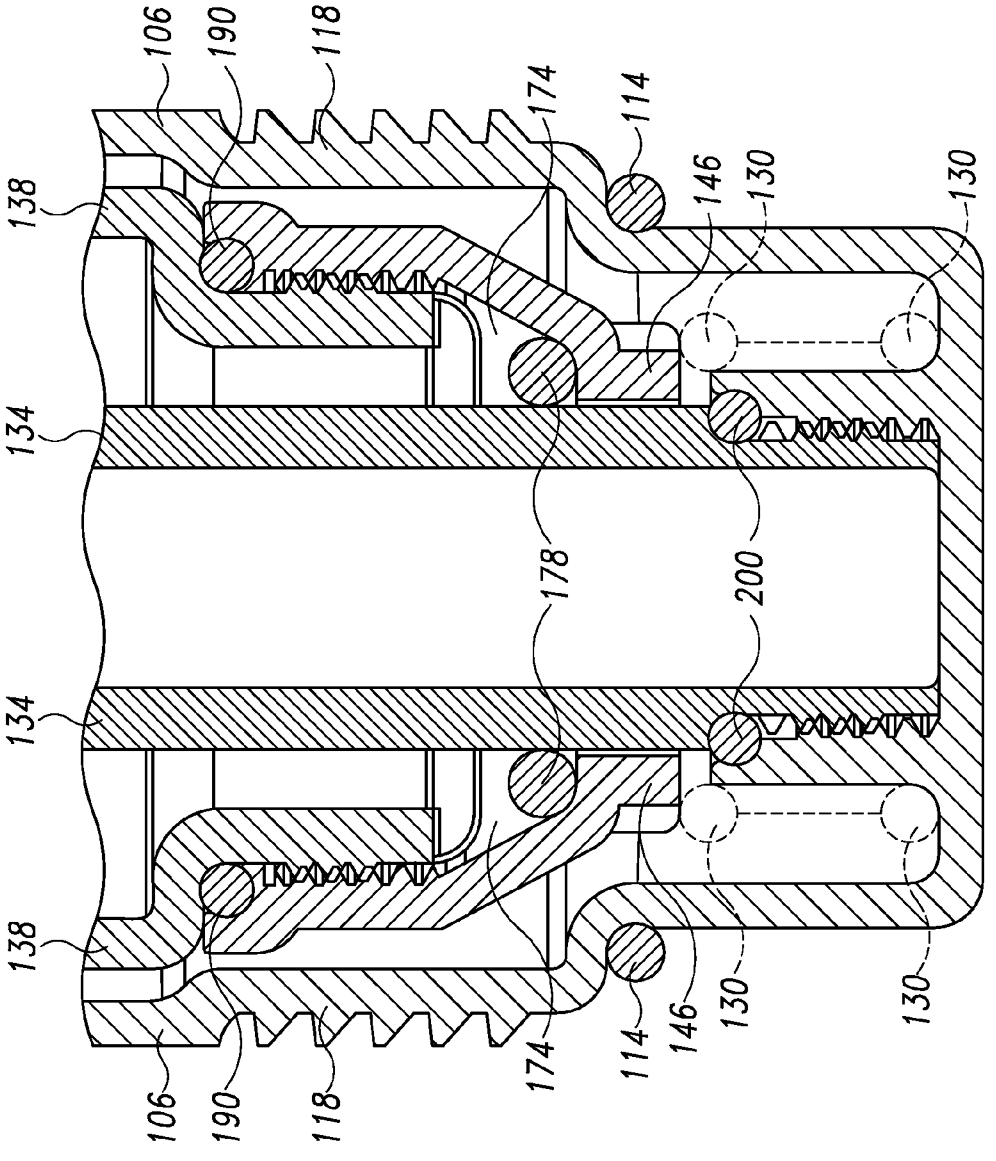
FIG. 8 depicts a cross-sectional view of a lower portion of the double action hand pump of FIG. 6.

Referring now to FIGS. 6 to 8, the housing 106 surrounds the pump mechanism and includes a threaded bottom portion 118 to secure the pump 30 to the threaded drain 60 in the cap 22. An o-ring 114 prevents the pressure developed in the container 34 from escaping through the junction between the drain 60 and the outer housing 106. The outer housing 106, pump mechanism, and of course the handle 110 remain outside of the container 34 when the pump 30 is connected to the cap 22. The length of the pump 30 combined with the height of the tank 14 enable a user to stroke the pump 30 without having to bend over excessively far on the downstroke, as compared to pressure sprayers that utilize a pump 30 submerged within the container 34.

The pump handle 110 is threadedly connected to the top of the pump cylinder 138, as illustrated in FIG. 7. The handle 110 includes a horizontal contact bar 112 that a user may grasp while stroking the pump 30. In one embodiment, the length of the contact bar 112 is slightly greater than the width of a man's hand, to permit a user to grasp the handle 110 and stroke pump 30 with a single hand. However, in another embodiment, the length of the contact bar 112 permits a man wearing work gloves to place his two hands side-by-side upon the contact bar 112 while stroking the pump. Additionally, the contact bar 112 includes a series of ridges that provide a gripping surface, and also make the handle 110 easier to hold, should the handle 110 become wet.

With continued reference to FIG. 7, the handle 110 can be secured to the outer housing 106 enabling a user to carry the tank sprayer 10 by the pump handle 110. The base of the handle 110 includes a tab 122 used to secure the handle 110 to the outer housing 106. The tab 122 engages a slot 126 in the outer housing 106 when the handle 110 is fully depressed and rotated. In one embodiment, a pump cushioning spring 130 must also be depressed in order to slide the tab 122 into the slot 126. The resistive force from the pump cushioning spring 130 presses the tab 122 against the top portion of the slot 126 ensuring the handle 110 remains in the locked position until the user desires to disengage the tab 122 from the slot 126 by rotating the handle 110.

The pump mechanism injects air into the container 34 for compression. The pump mechanism includes a central connecting rod 134, a pump cylinder 138, a primary piston 142, a secondary piston 146, first and second check valves 150, 154, and a plurality of sealing members and gaskets, as illustrated in FIG. 6. The interrelationship of each pump mechanism component is explained below.

With reference to FIG. 6, the central connecting rod 134 is a hollow tube that includes a bottom end in fluid communication with the container 34. The connecting rod 134 includes a top portion threadedly connected to the primary piston 142, and a bottom portion threadedly connected to the outer housing 106. O-ring 200 forms an air tight seal between the connecting rod 134 and the outer housing 106. O-ring 194 forms an air tight seal between primary piston 142 and the connecting rod 134. As explained within, the pump cylinder 138 forces air through the connecting rod 134 and into the container 34 for compression.

The pump cylinder 138 is a hollow tube that surrounds the central connecting rod 134. The pump cylinder 138 is made from a rigid material, usually plastic. As illustrated in FIG. 7, the pump cylinder 138 includes a top portion threadedly connected to the base of the handle 110, and, as illustrated in FIGS. 8A and 8B, a bottom portion threadedly connected to the secondary piston 146. An o-ring 190 ensures that the pump cylinder 138 makes an air tight junction with the secondary piston 146.

The primary piston 142 and the second check valve 154 are threadedly engaged to the top of the connecting rod 134, as illustrated in FIG. 7. The primary piston 134 has an outside diameter slightly smaller than the inside diameter of the pump cylinder 138. The primary piston 134 includes a groove 182, which houses a "floating" o-ring 186. The diameter of a cross section of the o-ring 186 is slightly smaller than the height of the groove 182, such that the o-ring 186 is vertically displaceable within the groove 182. As the pump 30 is stroked, the o-ring 186 moves to the top of the groove 182 on the upstroke, as illustrated by FIG. 10B, and moves to the bottom of the groove 182 on the downstroke, as illustrated by FIG. 10A.

With reference to FIG. 8, the secondary piston 146 is a circular ring threadedly engaged to the bottom of the pump cylinder 138. As the handle 110 is stroked, the pump cylinder 138 and the secondary piston 146 slide along the outer surface of the connecting rod 134. The secondary piston 146 includes a groove 174 which houses a "floating" o-ring 178. The diameter of a cross section of the o-ring 178 is slightly smaller than the height of the groove 174, such that the o-ring 178 is vertically displaceable within the groove 174. The o-ring 178 inside diameter is equal to the outside diameter of connecting rod 134. As the pump 30 is stroked, the o-ring 178 slides up and down the outer surface of the connecting rod 134, moving to the top of the groove 174 on the downstroke, as illustrated by FIG. 9A, and moving to the bottom of the groove 174 on the upstroke, as illustrated by FIG. 9B.

Check valves 150, 154 include bases 152, 156 with openings 158, 162 and elastomeric diaphragms 166, 170, as illustrated in FIG. 7. Each check valves 150, 154 selectively seals a cavity of varying size formed by the motion of the pump cylinder 138. When the air pressure above the check valves 150, 154 exceeds the air pressure below the check valve 150, 154 the edges of the diaphragm 166, 170 flex away from the base 152, 156 permitting air to travel to the area of lower pressure through the openings 158, 162. When the air pressure below the check valves 150, 154 exceeds the air pressure above the check valves 150, 154, the air pressure forces the edges of the diaphragm 166, 170 against the base 152, 156 thereby sealing the openings 158, 162.

Figure 9B:
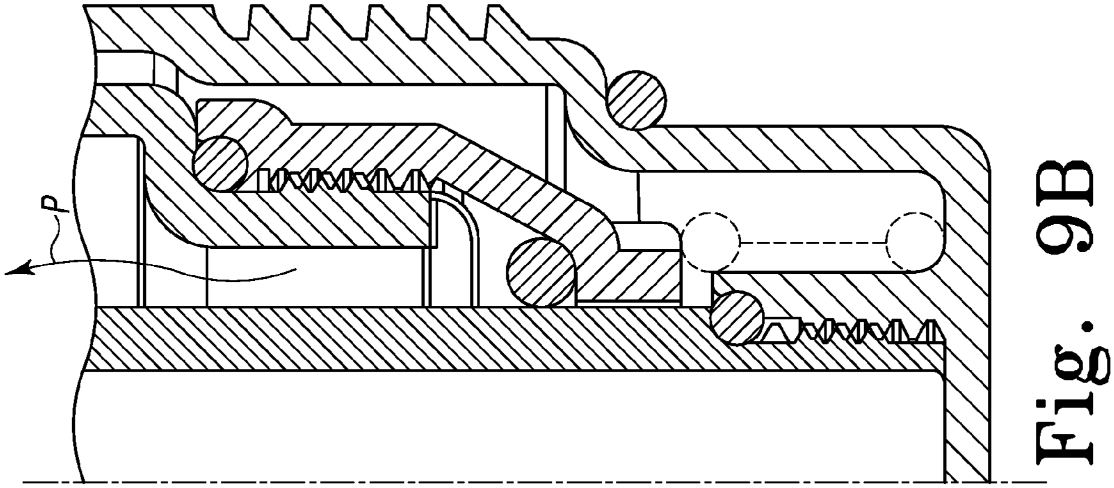
FIG. 9B depicts a cross-sectional view of the lower portion of the double action hand pump in the upstroke configuration.
Figure 10B:
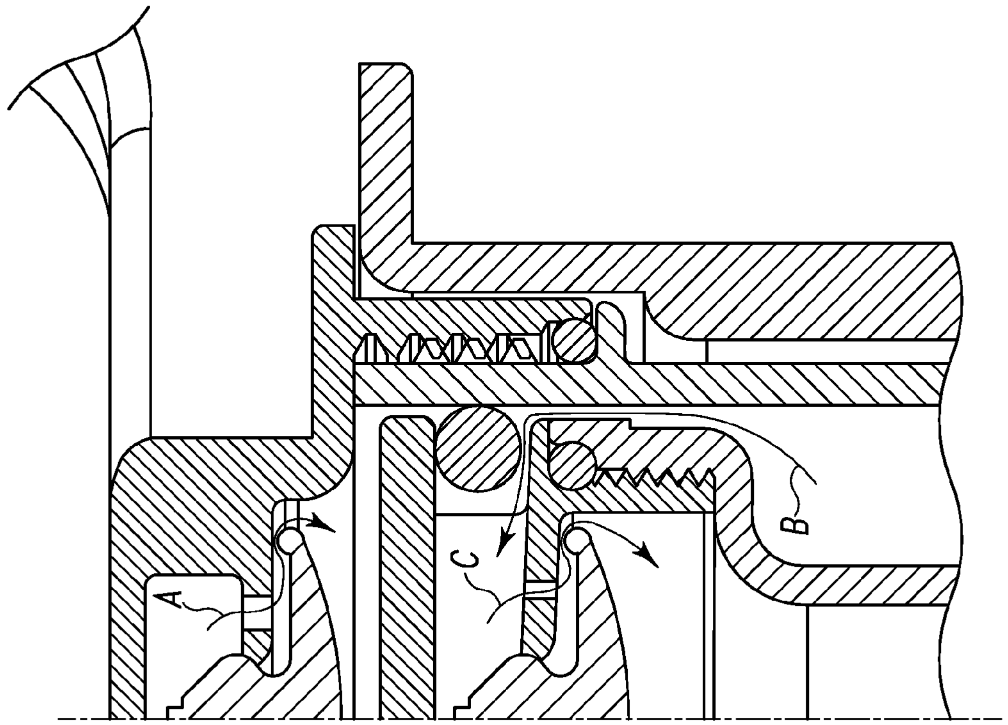
FIG. 10B depicts a cross-sectional view of the upper portion of the double action hand pump in the upstroke configuration.
Figure 10A:
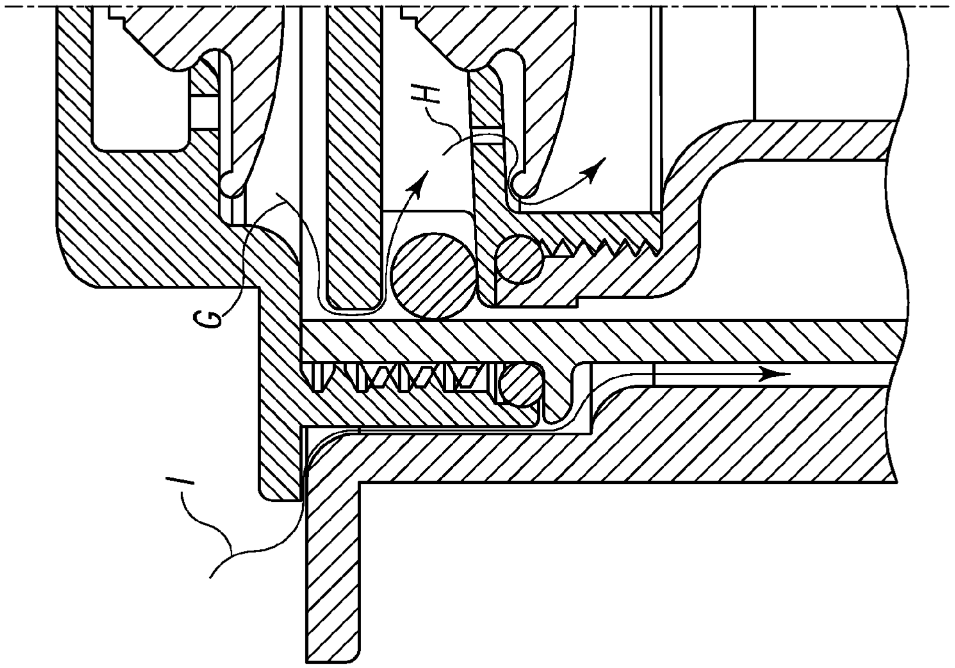
FIG. 10A depicts a cross-sectional view of the upper portion of the double action hand pump in the downstroke configuration.

When a user initiates an upstroke, as illustrated in FIGS. 9B and 10B, by forcing the handle 110 and the pump cylinder 138 upward, the second check valve 154 opens allowing outside air to flow along direction A into the cavity defined at the top by the second check valve 154 and at the bottom by the primary piston 142. Air continues to flow through the second check valve 154 into the aforementioned cavity throughout the entire upstroke motion. Additionally, the upstroke draws o-ring 186 against the top side of the groove 182 in the primary piston 142, and o-ring 178 against the bottom side of the groove 174 in the secondary piston 146. As the upward motion of the pump cylinder 138 causes the cavity between the pump cylinder 138 and the connecting rod 134 to become smaller, the air within the cavity is forced into groove 182 along directions P and B. After passing through the groove 182 the air flows along direction C, into the openings 158 in the first check valve 150. Finally, the air flows into the connecting rod 134, and ultimately into the container 34 for compression.

Figure 9A:
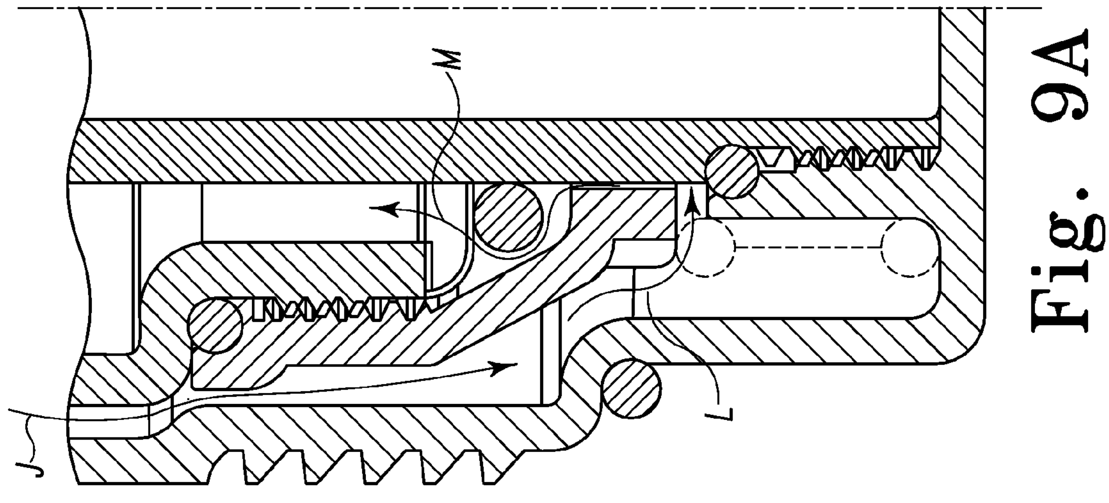
FIG. 9A depicts a cross-sectional view of the lower portion of the double action hand pump in the downstroke configuration.

Alternatively, when a user initiates a downstroke, as illustrated in FIGS. 9A and 10A, by forcing the handle 110 and the pump cylinder 138 downward, the air trapped above the primary piston 142 forces the second check valve 154 closed, and o-ring 186 to the bottom of the groove 182 in the primary piston 142. As the downward motion of the pump cylinder 138 causes the cavity above the primary piston 142 to become smaller, the air within the cavity is forced into groove 182 along direction G. Throughout the downstroke the air continues to flow, along direction H, through the openings 158 in the first check valve 150, into the connecting rod 134, and ultimately into the container 34.

Also during the downstroke, the downward motion of the pump cylinder 138 forces o-ring 178 to the top of the groove 174 in the secondary piston 146, permitting air to enter the cavity between the pump cylinder 138 and the connecting rod 134, in the following manner. First, the downward motion develops a vacuum between the pump housing 106 and the pump cylinder 138 that draws in outside air along directions I and J. Next, the air is drawn around the pump cushioning spring 130 along direction L. Finally, the vacuum draws air between the secondary piston 146 and the connecting rod 134, and through groove 174, along direction M. In summary, the pump 30 includes two air chambers; during each pump 30 stroke one of the chambers is filled with outside air, while the air in the other chamber is evacuated into container 34. Thereby, enabling the pump to deliver air to the container 34 during each pump 30 stroke.

After a series of pump 30 strokes, the user will have pumped a substantial volume of air into the container 34. The air pressure generated by the increased volume of air forces the diaphragm 166 of the first check valve 150 to seat against the base 152, thereby indefinitely maintaining the volume of air within the container 34. When the user activates the valve on the spray wand the increased air pressure propels the solution from the container 34.

To reduce the probability of the pump 30 becoming damaged due to vigorous downward stroking, the pump 30 includes a cushioning spring 130. The bottom surface of the cushioning spring 130 contacts the bottom of the pump housing 106, and the top of the spring 130 contacts the bottom portion of the secondary piston 146. The spring 130 cushions the secondary piston 146 should the piston 146 become forcefully directed toward the bottom of the pump 30. Additionally, the cushioning spring 130 provides tension upon the handle 110 when the handle 110 is in the locked position.

In operation, a user first obtains and utilizes appropriate safety attire, which may include safety glasses, gloves, apron, and face mask. Next, the user places his or her shoes in the footholds 54, 55, grasps the pump handle 110, and slowly rotates the handle 110 until the pump 30 can be removed from the cap 22. Then, with shoes remaining in the footholds 54, 55, the user grasps the cap handles 58, 59 and rotates the cap 22 until it can be removed from the container 34. Alternatively, the user may stand upon the footstands 50, 51 when removing the cap 22 from the container 34. With the cap 22 removed, the user can clean the inside of the container 34 or fill the container 34 with an appropriate amount of water or other solvent. Next, the user tightly secures the cap 22 to the container 34, using the footholds 54, 55 to stabilize the container 34. If the user desires to add a solute to the solvent, the user can measure an appropriate quantity of solute in the measuring cup 26. When the appropriate amount of solute has been measured, the user pivots the measuring cup 26 to the tilted "pour" position to direct the solute onto the surface of the funnel 62 through the drain 60 in the cap 22 and into the container 34. Next, the user attaches the pump 30 to the threaded drain 60. Finally, the user stands upon the footstands 50, 51 and repeatedly strokes the pump 30 until a sufficient air pressure has been developed in the container 34. Likewise, the user may stabilize the tank 14 with the footholds 54, 55 while stroking the pump 30. Finally, the user may the trigger the spray wand to distribute the product, following any and all directions provided by the manufacturer of the solvent or solute.

Those skilled in the art will recognize that numerous modifications can be made to the specific implementations described above. Therefore, the following claims are not to be limited to the specific embodiments illustrated and described above. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants, patentees, and others.

What is claimed is:

1. A tank sprayer, comprising:

a tank configured to hold fluid therein, said tank having (i) an upper portion defining a tank opening and a first threaded portion, and (ii) a lower portion;

a cap having (i) a skirt defining a second threaded portion configured to mate with said first threaded portion of said tank so as to secure said cap to said tank over said tank opening, (ii) a central portion attached to said skirt and defining a third threaded portion configured to form a fluid passage, and (iii) at least one handle attached to said skirt;

a double acting hand pump configured to pressurize said tank with air on both an upstroke and a downstroke, said pump having a fourth threaded portion configured to mate with said third threaded portion of said central portion of said cap so as to secure said pump to said cap;

a first footstand attached to said lower portion of said tank, said first footstand extending laterally outwardly from said tank; and a second footstand attached to said lower portion of said tank, said second footstand extending laterally outwardly from said tank, and said second footstand being spaced apart from said first footstand, wherein said first footstand includes a first lateral sidewall and a second lateral sidewall spaced apart from each other, wherein said second footstand includes a third lateral sidewall and a fourth lateral sidewall spaced apart from each other, wherein said tank sprayer includes (i) a first concave foothold structure that includes at least said first lateral sidewall and said third lateral sidewall, and (ii) a second concave foothold structure that includes at least said second lateral sidewall and said fourth lateral sidewall, wherein said first concave foothold structure defines a first recess, wherein said second concave foothold structure defines a second recess, and wherein each of said first recess and said second recess is configured to receive at least a portion of a user's foot therein.

2. The tank sprayer of claim 1, wherein:

said first footstand extends in a first direction laterally away from said lower portion of said tank, said second footstand extends in a second direction laterally away from said lower portion of said tank, and said first direction is substantially opposite said second direction.

3. The tank sprayer of claim 1, wherein a width of said first recess is about 4 to 6 inches.

4. The tank sprayer of claim 3, wherein a depth of said first recess is about 2 to 3 inches.

5. The tank sprayer of claim 4, wherein a height of said first recess is about 1 to 2 inches.

6. The tank sprayer of claim 1, wherein:

said first footstand includes a first gripping structure on a first upper surface of said first footstand, and said second footstand includes a second gripping structure on a second upper surface of said second footstand.

7. The tank sprayer of claim 1, wherein:

said cap has a plurality of handles which includes said at least one handle, and said plurality of handles includes (i) a first handle extending from said skirt, and (ii) a second handle spaced apart from said first handle and extending from said skirt.

8. The tank sprayer of claim 1, wherein:

said first handle extends from said skirt in a first direction, and said second handle extends from said skirt in a second direction which is substantially opposite said first direction.

9. The tank sprayer of claim 1, wherein:

said first threaded portion is externally threaded, said second threaded portion is internally threaded, said third threaded portion is internally threaded, and said fourth threaded portion is externally threaded.

* * * * *